(12) United States Patent
Ryu et al.

(10) Patent No.: US 9,327,131 B2
(45) Date of Patent: May 3, 2016

(54) DETECTING IMPLANTED MEDICAL ELECTRICAL LEAD DISLODGEMENT USING CARDIAC SIGNALS

(75) Inventors: Kyungmoo Ryu, Palmdale, CA (US); Stuart Rosenberg, Castaic, CA (US); Edward Karst, South Pasadena, CA (US)

(73) Assignee: PACESETTER, INC., Sylmar, CA (US)

( * ) Notice: Subject to any disclaimer, the term of this patent is extended or adjusted under 35 U.S.C. 154(b) by 396 days.

(21) Appl. No.: 12/961,065

(22) Filed: Dec. 6, 2010

(65) Prior Publication Data

US 2012/0143278 A1    Jun. 7, 2012

(51) Int. Cl.
| | |
|---|---|
| *A61N 1/37* | (2006.01) |
| *A61B 5/0452* | (2006.01) |
| *A61B 5/08* | (2006.01) |
| *A61B 5/11* | (2006.01) |
| *A61B 5/00* | (2006.01) |
| *A61N 1/39* | (2006.01) |
| *A61N 1/08* | (2006.01) |

(52) U.S. Cl.
CPC .............. *A61N 1/37* (2013.01); *A61B 5/04525* (2013.01); *A61B 5/0816* (2013.01); *A61B 5/1116* (2013.01); *A61B 5/7292* (2013.01); *A61B 2560/0276* (2013.01); *A61N 1/3956* (2013.01); *A61N 2001/083* (2013.01)

(58) Field of Classification Search
CPC ............. A61B 5/0402; A61B 5/04023; A61B 5/04024; A61B 5/04028
USPC ...................................................... 607/27, 28
See application file for complete search history.

(56) References Cited

U.S. PATENT DOCUMENTS

| | | | |
|---|---|---|---|
| 6,112,119 A * | 8/2000 | Schuelke et al. ................... 607/9 |
| 6,347,249 B1 * | 2/2002 | Kim et al. ......................... 607/27 |
| 6,721,600 B2 * | 4/2004 | Jorgenson et al. ............... 607/27 |
| 7,515,961 B2 | 4/2009 | Germanson et al. |
| 7,664,550 B2 * | 2/2010 | Eick et al. ......................... 607/27 |
| 2002/0120307 A1 | 8/2002 | Jorgenson et al. |
| 2004/0162593 A1 | 8/2004 | Jorgenson et al. |
| 2006/0247706 A1 | 11/2006 | Germanson et al. |
| 2007/0270914 A1 | 11/2007 | Vincent et al. |
| 2009/0299421 A1 * | 12/2009 | Sawchuk ........................... 607/4 |

FOREIGN PATENT DOCUMENTS

| | | |
|---|---|---|
| WO | 03077822 A2 | 9/2003 |
| WO | 03077822 A3 | 1/2004 |
| WO | 2006118762 A1 | 11/2006 |
| WO | 2009148427 A1 | 12/2009 |

* cited by examiner

*Primary Examiner* — Joseph Dietrich

(57) ABSTRACT

Evaluation of an implanted electrical lead condition includes comparing electrogram template features with test electrogram features. The evaluating also includes determining the implanted electrical lead condition based solely on the electrogram comparison. The compared test electrogram features and template electrogram features may be atrial amplitudes and ventricular amplitudes. The sensing may be with a quad polar lead. The compared test electrogram features and electrogram template features may account for different patient postures and/or may account for respiration modulation.

19 Claims, 7 Drawing Sheets

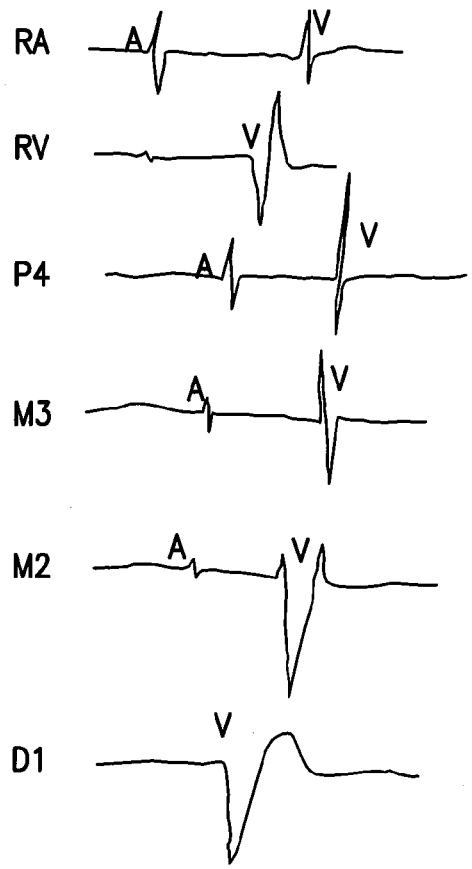
FIG. 3
FIG. 4
A = 2 mVA = 1.9 mV
V = 4 mVV = 4.1 mV
A/V = 0.5A/V = 0.46

A = 2 mV
V = 4 mV
A/V = 0.5

A = 3 mV
V = 3 mV
A/V = 1.0

A = 2 mV
V = 4 mV
A/V = 0.5

A = 2mV
V = 3 mV
A/V = 0.67

A = 2 mV
V = 4 mV
A/V = 0.5

A = 1mV
V = 4mV
A/V = 0.25

| | A amplitude increased | A amplitude decreased | A amplitude not changed |
|---|---|---|---|
| A/V Ratio Increased | Likely Dislodgment | | |
| A/V Ratio Decreased | | New Atrial Substrate? | New Ventricular Substrate? |

FIG. 9

DETECTING IMPLANTED MEDICAL ELECTRICAL LEAD DISLODGEMENT USING CARDIAC SIGNALS

FIELD OF THE DISCLOSURE

The present disclosure relates, in general, to implantable medical devices and, more particularly, to detecting electrical lead dislodgement using cardiac signals.

BACKGROUND

An implantable medical device (IMD), such as a pacemaker and/or implantable cardioverter-defibrillator (ICD), regulates or synchronizes the beating of the heart with electrical impulses, delivered by electrical leads having electrodes contacting the heart muscles. Some IMDs include a number of different sensors and logic allowing them to monitor the rate and rhythm of the heart as well as to measure various cardiac surrogates that provide information on the operation of the heart.

Cardiac resynchronization therapy (CRT) often employs a left ventricular lead placed via the coronary sinus. The electrical lead itself is typically small and has some curvature to achieve passive fixation, i.e., not actually anchoring into the myocardium. Rather than relying on anchoring, the shape of the lead attempts to hold the lead in place. Due to movement of the patient and also cardiac motion (even when the patient is not moving) the lead may dislodge from the location where the physician had implanted it. Moreover, in some lead implant sites, e.g., in the coronary venous system of the heart, counter flowing blood could also promote dislodgement.

Dislodgement of pacing leads, particularly the passively-fixated left ventricle leads in the coronary sinus, is viewed as a risk associated with the CRT implant procedure. Sometimes due to patient anatomy and/or limitations of leads and delivery tools, it is difficult to place the lead in a stable location that avoids phrenic nerve stimulation and that provides adequate cardiac resynchronization when paced. Patient posture in the hours following implant can exacerbate problems with lead stability. Even between the subacute period and to several weeks post-procedure, the course of time, in which fibrosis/tissue in-growth "locks" the lead in place, is not well known. Finally, with cardiac remodeling due to progressively worsening heart failure or due to reverse remodeling from efficacious therapies, it is possible for a lead to migrate with time.

Although impedance can be used to detect lead dislodgment, impedance is not entirely reliable. For example, impendence varies over the first several days after implant, as well as when the lead matures. Moreover, if the lead stabilizes in a new location, then the impedance may not appear to change substantially, thus, hindering detection of lead migration.

Fluoroscopic procedures can detect a macro dislodgement (e.g., five to ten millimeters) but such procedures expose a patient and the physician to further radiation through the fluoroscope x-rays. Moreover, fluoroscopy may not detect micro dislodgment.

SUMMARY

Using a pacing lead, such as a quad polar lead which has four electrodes in the coronary sinus, a number of signals can be analyzed. For example, relative amplitudes of the atrial components and the ventricular components of an electrogram can indicate whether the lead is stable or has dislodged.

Using a quad polar left ventricular lead, both left ventricular and left atrial electrograms can be sensed. In particular, it is expected that for many lead placements (i.e., for most patients in most coronary sinus branches) the proximal electrode (P4), when configured in unipolar sensing, will produce an electrogram with both atrial and ventricular potentials. One aspect of the present disclosure looks at the long term trend of the amplitude of the atrial and ventricular potentials on the electrogram, as well as the trend of the ratio of atrial to ventricular amplitudes, as an index of lead stability. Based on the trends of the atrial amplitude and the A/V ratio (described in more detail below), a determination is made as to whether the lead is stable, the lead has dislodged, or the underlying substrate has changed.

According to an aspect of the present disclosure, a method for evaluating an implanted electrical lead condition includes comparing electrogram template features with test electrogram features. The method also includes determining the implanted electrical lead condition based solely on the electrogram comparison.

In another aspect, an implantable medical device (IMD) includes at least one electrical lead and a programmable microcontroller coupled to the electrical lead(s). The programmable microcontroller controls operation of the IMD. The IMD also has a memory coupled to the programmable microcontroller. The memory stores an electrogram template, and a lead condition analysis module. When executed by the programmable microcontroller, the lead condition analysis module configures the IMD to compare the electrogram template with test electrogram features, and to determine an electrical lead condition based solely on the electrogram comparison.

In yet another aspect, a system for evaluating an implanted electrical lead condition has means for comparing electrogram template features with test electrogram features. The system also has means for determining the implanted electrical lead condition based solely on the electrogram comparison.

In a further aspect, a method for evaluating an implanted electrical lead condition includes comparing atrial and ventricular features of an electrogram template with atrial and ventricular features of a test electrogram. The method also includes determining the implanted electrical lead condition based on the comparison.

In a still further aspect, an implantable medical device (IMD) has at least one electrical lead, and a programmable microcontroller coupled to the electrical lead(s). The programmable microcontroller controls operation of the IMD. The IMD also has a memory coupled to the programmable microcontroller, the memory storing a lead condition analysis module. When executed by the programmable microcontroller, the lead condition analysis module configures the IMD to compare atrial and ventricular features of an electrogram template with atrial and ventricular features of a test electrogram, and to determine an electrical lead condition based on the comparison The foregoing has outlined rather broadly the features and technical advantages of the present teachings in order that the detailed description of the teachings that follows may be better understood. Additional features and advantages of the teachings will be described hereinafter which form the subject of the claims of the teachings. It should be appreciated by those skilled in the art that the conception and specific embodiment disclosed may be readily utilized as a basis for modifying or designing other structures for carrying out the same purposes of the present teachings. It should also be realized by those skilled in the art that such equivalent constructions do not depart from the spirit and scope of the teachings as set forth in the appended claims. The novel features which are believed to be characteristic of the teachings, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present teachings.

BRIEF DESCRIPTION OF THE DRAWINGS

For a more complete understanding of the present teachings, reference is now made to the following descriptions taken in conjunction with the accompanying drawing.

FIG. 3 is a diagram illustrating exemplary intra cardiac electrograms, recorded from a variety of locations, showing atrial and ventricular potentials.

FIG. 4 is a diagram illustrating exemplary baseline and test intra cardiac electrograms, recorded from a left ventricular quad polar lead, showing atrial and ventricular potentials.

FIG. 9 is an exemplary table of lead diagnoses.

DETAILED DESCRIPTION

The following description includes the best mode presently contemplated for practicing the present teachings. The description is not to be taken in a limiting sense but is merely for the purpose of describing the general principles of the illustrative embodiments. The scope of the present teachings should be ascertained with reference to the claims. In the description that follows, like numerals or reference designators will refer to like parts or elements throughout.

Overview of Implantable Devices

Figure 1:
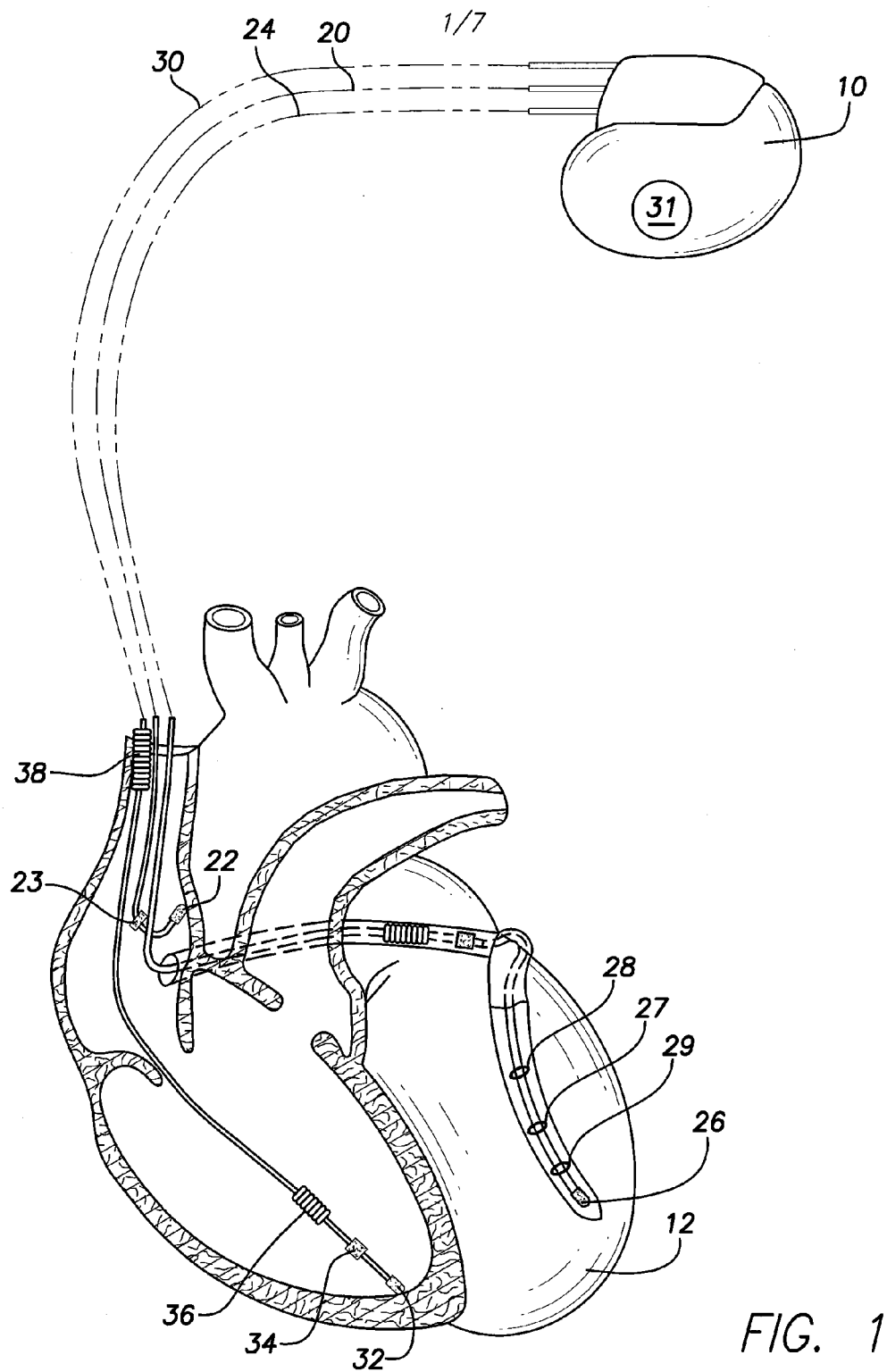
FIG. 1 is a diagram illustrating a medical device in electrical communication with the heart of a patient by way of three leads suitable for delivering multi-chamber stimulation and shock therapy.

With reference to FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage, and an atrial ring electrode 23.

To sense left atrial and ventricular cardiac signals and to provide left chamber pacing therapy, the stimulation device 10 is coupled to a quad pole lead 24 designed for placement in the latero or postero-lateral branch of the left ventricle via the coronary sinus. Accordingly, an exemplary quad pole lead 24 is designed to receive atrial and ventricular cardiac signals and to deliver left heart pacing therapy using at least a left ventricular distal electrode (D1) 26, mid first ring (M2) 29, mid second ring (M3) 27 and proximal ring (P4) 28. The inter-electrode spacing, in one embodiment, is 20 mm (D1-M2), 10 mm (M2-M3), and 17 mm (M3-P4). Thus, from tip to proximal the lead spans 47 mm. When the tip is pushed as far as anatomically possible in a coronary sinus branch, the proximal ring is often near the atrial-ventricular (AV) groove and sometimes even in the main coronary sinus or Great Cardiac Vein instead of the branch. The unipolar P4-RV coil sense vector, the bipolar M3-P4 sense vector, and sometimes additional unipolar and bipolar vectors, display both atrial and ventricular potentials on the electrogram. In one embodiment, the mid second ring (M3) 27 and the proximal ring (P4) 28 represent electrical signals of the left atrium.

As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart so as to place the right ventricular tip electrode 32 in the right ventricular apex so the RV coil electrode 36 is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "vibratory alert" signal (from a motor with an offset mass that can be provided in the device can), an additional electrode 31 can be provided in proximity to the device can.

Figure 2:
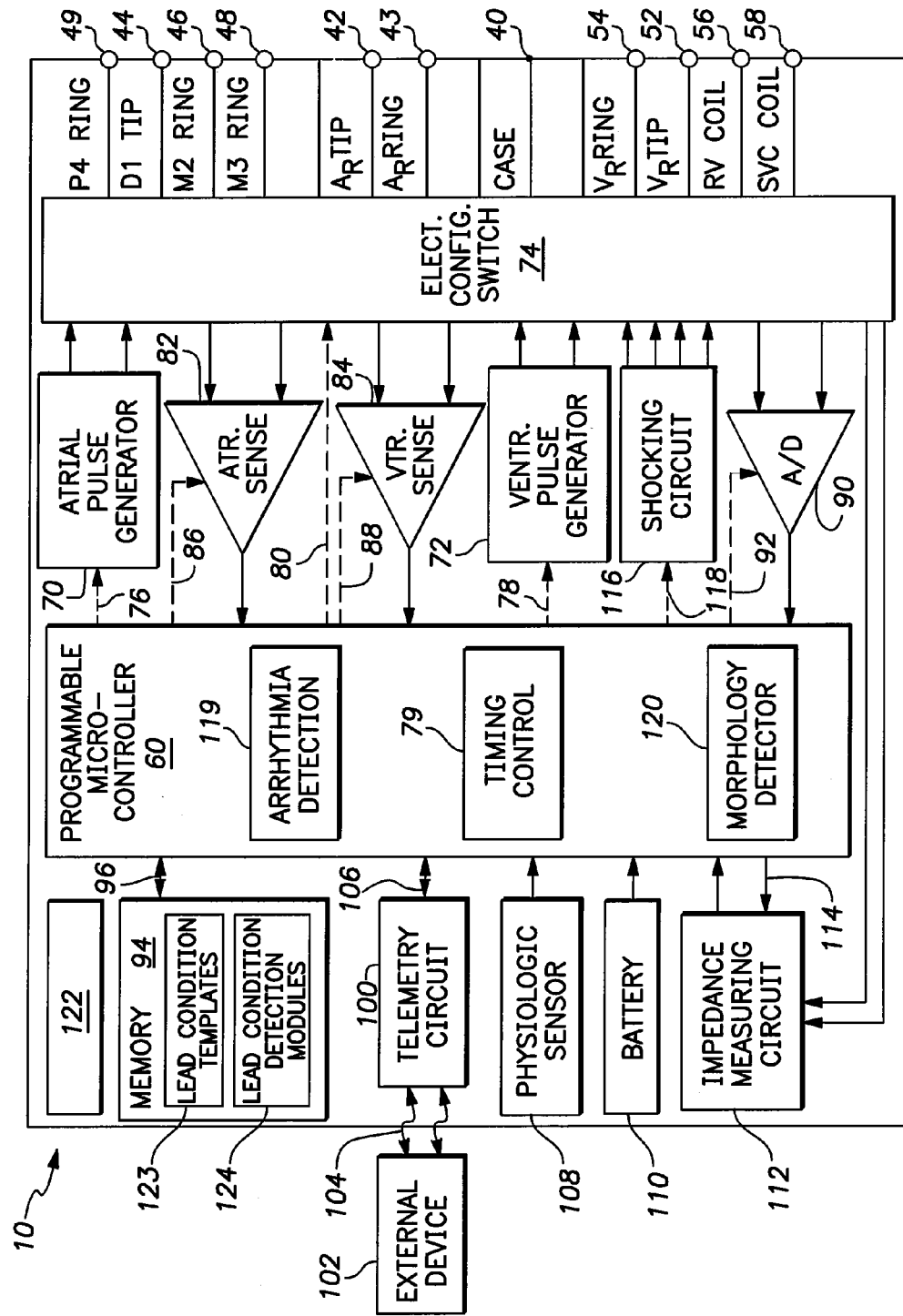
FIG. 2 is a block diagram illustrating an implantable medical device configured as a system in which the various embodiments of the present teachings may operate.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. The stimulation device 10 is configured as a system in which the various embodiments of the present teachings may operate. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes 36 and 38, (FIG. 1) for shocking purposes. The housing 40 further includes a connector (not shown) having terminals, 42, 43, 44, 46, 48, 49, 52, 54, 56 and 58 (shown schematically and, for convenience, the names of the electrodes to which they are connected are shown next to the terminals).

As such, to achieve right atrial sensing and pacing, the connector includes at least a right atrial tip terminal (AR TIP) 42 adapted for connection to the atrial tip electrode 22 (FIG. 1) and a right atrial ring (AR RING) electrode 43 adapted for connection to the right atrial ring electrode 23 (FIG. 1). To achieve left chamber sensing and pacing, the connector includes at least a left ventricular tip terminal (D1 TIP) 44, a left ventricular ring terminal (M2 RING) 46, a left heart ring terminal (M3 RING) 48, and a left heart proximal terminal (P4 RING) 49, which are adapted for connection to the left ventricular distal electrode (D1) 26 (FIG. 1), the mid first ring (M2) 29 (FIG. 1), the mid second ring (M3) 27 (FIG. 1) and the proximal ring (P4) 28 (FIG. 1), respectively. As noted previously, the mid second ring (M3) 27 and the proximal ring (P4) 28 are possibly located in the left ventricle or the left atrium.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32 (FIG. 1), right ventricular ring electrode 34 (FIG. 1), the RV coil electrode 36 (FIG. 1), and the SVC coil electrode 38 (FIG. 1), respectively. To provide the "vibratory alert" signal, a vibratory alert unit 122 generates a signal for an additional terminal (not shown) for connection to the vibratory alert electrode 31 (FIG. 1). In one embodiment, the vibratory alert will alert the patient, and then a home monitor can be used to transfer the information associated with the alert from the device 10 to an attending medical professional, who can take the appropriate clinical action.

At the core of the stimulation device 10 is a programmable microcontroller 60, which controls the various modes of stimulation therapy. As is well known in the art, the microcontroller 60 (also referred to as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. The microcontroller 60 includes the ability to process or monitor input signals (data) as controlled by program code stored in a designated block of the memory. The details of the design and operation of the microcontroller 60 are not critical to the present teachings. Rather, any suitable microcontroller 60 may be used that carries out the functions described. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20 (FIG. 1), the right ventricular lead 30 (FIG. 1), and/or the quad pole lead 24 (FIG. 1) via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 that controls the timing of such stimulation pulses (e.g., pacing rate, atrioventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., as is well known in the art. The switch 74 includes multiple switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20 (FIG. 1), the quad pole lead 24 (FIG. 1), and the right ventricular lead 30 (FIG. 1), through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers and may receive control signals 86, 88 from the controller 60. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, band pass filtering, and a threshold detection circuit, as known in the art, to selectively sense the cardiac signal of interest. The automatic gain control enables the device 10 to effectively address the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks).

Cardiac signals are also applied to the inputs of an analog-to-digital (A/D) data acquisition system 90. The data acquisition system 90 is configured to acquire intra-cardiac electrogram (IEGM) signals, convert the raw analog data into a digital signal, and store the digital signals for later processing and/or telemetric transmission to an external device 102. The data acquisition system 90 is coupled to the right atrial lead 20 (FIG. 1), the quad pole lead 24 (FIG. 1), and the right ventricular lead 30 (FIG. 1) through the switch 74 to sample cardiac signals across any pair of desired electrodes. The controller 60 controls the data acquisition system via control signals 92.

The microcontroller 60 is further coupled to a memory 94 by a suitable data/address bus 96. The programmable operating parameters used by the microcontroller 60 are stored and modified, as required, in order to customize the operation of the stimulation device 10 to suit the needs of a particular patient. The memory 94 stores lead condition templates 123, and lead condition detection modules 124 which, when used by the microcontroller 60, provide the operational functions of the implantable stimulation device 10, as described in more detail below. Additional operating parameters and code stored on the memory 94 define, for example, pacing pulse amplitude or magnitude, pulse duration, electrode polarity, rate, sensitivity, automatic features, arrhythmia detection criteria, and the amplitude, wave shape and vector of each shocking pulse to be delivered to the patient's heart within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, trans-telephonic transceiver, a diagnostic system analyzer, or even a cellular telephone. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In one embodiment, the stimulation device 10 further includes a physiologic sensor 108, commonly referred to as a "rate-responsive" sensor because it adjusts pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 is capable of operating at low current drains for long periods of time, and is capable of providing high-current pulses (for capacitor charging) when the patient requires a shock pulse. The battery 110 also has a predictable discharge characteristic so that elective replacement time can be detected. In one embodiment, the device 10 employs lithium/silver vanadium oxide batteries. As further shown in FIG. 2, the device 10 has an impedance measuring circuit 112 enabled by the microcontroller 60 via a control signal 114.

In the case where the stimulation device 10 is intended to operate as an IMD, it detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the RV coil electrode 36 (FIG. 1), the SVC coil electrode 38 (FIG. 1) and the case 10. Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The microcontroller 60 includes a morphology detector 120 for tracking various morphological features within electrical cardiac signals, including intervals between polarization events, elevations between polarization events, durations of polarization events and amplitudes of polarization events. The microcontroller 60 also includes an arrhythmia detection control 119 that analyzes the sensed electrical signals to determine whether or not arrhythmia is being experienced.

The remaining figures, flow charts, graphs and other diagrams illustrate the operation and novel features of the stimulation device 10 as configured in accordance with exemplary embodiments of the present teachings. In the flow chart, the various process steps are summarized in individual "blocks." Such blocks describe specific actions or decisions made or carried out as the process proceeds. Where a microcontroller (or equivalent) is employed, the functional block diagrams provide the basis for a "VA coupling analysis process" that may be used by such a microcontroller (or equivalent) to adaptively select RPC settings in IMD patients. Those skilled in the art may readily write such a program based on the functional block diagrams and other descriptions presented herein.

Determining Lead Condition

Based on the choice of various unipolar or bipolar sensing vectors, such as those newly enabled with a quad polar lead, and based on a position of the lead in the coronary venous system, sensed electrograms offer information about depolarization of the myocardium localized to specific regions of the left ventricle, global ventricular activation, and even atrial activation. Because of the positioning of a lead, such as the quad pole lead 24, the unipolar P4-RV coil sense vector, the bipolar M3-P4 sense vector, and sometimes additional unipolar and bipolar vectors, display both atrial and ventricular potentials on the electrogram. Such sensing ability facilitates determining a condition of the lead 24, for example to identify lead dislodgement. Although the present description mainly focuses on a quad polar lead, it is not so limited. Rather, any type of sensing lead is contemplated and falls within the scope of the present disclosure.

FIG. 3 is a diagram illustrating exemplary intra cardiac electrograms (IEGMs), recorded from a variety of locations, showing atrial and ventricular potentials. The topmost IEGM illustrates readings from a right atrial bipolar (RA) lead. The next IEGM illustrates readings from a right ventricular bipolar (RV) lead. The next four IEGMs illustrate readings from the left ventricular (LV) quad pole lead (P4, M3, M2, D1) including unipolar measurements to the right ventricular (RV) coil. Of course, the measurements could also have the RV ring, RA ring, SVC coil, can or common anode as the return electrode or any other sense configuration that senses both A and V potentials. Although the left ventricle (LV) is described throughout this application, the locations of the electrodes are not necessarily in the left ventricle.

For one cardiac cycle each of the leads senses one or more potentials that can be assigned to either an atrial bipolarization or a ventricular bipolarization. For the right atrial (RA) lead IEGM a first sharp spike indicates a local atrial potential (A wave). A lower frequency spike indicates a far field ventricular potential (V wave).

The right ventricular (RV) IEGM shows a very small peak (not labeled) indicating a far field atrial signal (A wave). In some cases this far field A wave is not present. A large peak indicates a ventricular potential (V wave) in the right ventricle.

On each of the left ventricular (LV) IEGMs, labeled LVP4, LVM3, LVM2, and LVD1 from top to bottom, one or more potentials is seen. P4 is a proximal electrode which is closer to the AV groove. D1 is the distal electrode which is closest to the LV apex. It is seen that the ventricular activation starts near the D1 electrode and moves from apex to base and, thus, the ventricular potential is seen as traveling. From the P4 and M3 electrodes, clearly there are both A and V potentials, as are visible on the LVP4 and LVM3 IEGMs. On the D1 electrode, no atrial potential is seen in the LVD1 because the D1 electrode is far from the atria, and the atrial mass is small. Development of a small atrial potential (A wave) is seen, in this example, on the M2 electrode at the LVM2 IEGM that may not be sensed by the device sense amplifier. The A wave grows increasingly large on the M3 and P4 electrodes, as shown in the LVM3 and LVP4 IEGMs. Moreover, the timing is slightly different. Thus, FIG. 3 illustrates timing and relative signal amplitudes on each of these electrodes for an A potential and a V potential.

According to an aspect of the present disclosure, when a lead is in a desired location, an electrode can obtain a relative measurement of the amplitudes of the A and V waves. The P4 electrode is a good example of an electrode with both atrial and ventricular potentials due to its location, but other electrodes could be used as well. The amplitude of the A wave and the amplitude of the V wave on the electrode can be stored in a template providing a baseline index of where that electrode is in relation to ventricular and atrial myocardia. In one embodiment, the baseline measurements occur when implanting the IMD and the lead is in the desired location.

At subsequent follow ups, either on demand or at regular automated intervals for periodic monitoring, new (TEST_N, where N is the follow-up number/sequence) amplitudes of the A and V potentials on the P4 electrogram LVP4 are stored. The amplitudes of the A potential at BASELINE and TEST_N are compared, as are the trend of the A/V ratios (amplitude) at BASELINE and TEST_N. It is also possible to compare the amplitude of the V potential at BASELINE and TEST_N. In another embodiment, the right ventricular (RV) IEGM is compared for the ratio calculation (i.e., A from P4 electrode and V from RV IEGM). A determination of lead stability is based on analysis of the data.

For example, if the A amplitude has remained the same, and the A/V ratio has remained the same, the lead is judged to be stable, that is, not dislodged. As seen in FIG. 4, the baseline measurements on the left show a 2.0 mV atrial potential and a 4.0 mV ventricular potential. The A/V ratio is 0.5. Over the course of time, as the lead matures and the patient's disease state changes (e.g., healthier or sicker) the amplitudes of each of those signals might change slightly. On the right hand side, test data (TEST_1) is seen, which was obtained some time after the baseline data was recorded. The atrial potential is 1.9 mV and the ventricular potential is 4.1 mV. The amplitudes have changed a little, but not much. The test A/V ratio is 0.46, which is very near the baseline 0.5 A/V. Consequently, it is diagnosed that this lead is likely in a stable position. That is, because the AV ratio is equal or nearly equal (i.e., within a certain threshold of change), the lead is deemed to be in a stable position.

Figure 5:
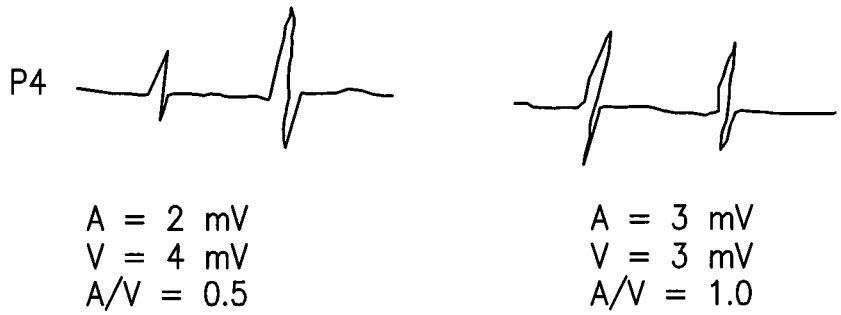
FIG. 5 is a diagram illustrating exemplary baseline and test intra cardiac electrograms, recorded from a left ventricular quad polar lead, showing atrial and ventricular potentials.

If the A amplitude has increased, and the A/V ratio has increased, it is more likely that the lead has dislodged and is getting pulled more proximal from its original position. FIG. 5 shows the same baseline A/V ratio of 0.5. On the right-hand side, the test data (TEST_2) shows the atrial amplitude has increased substantially to 3.0 mV and the ventricular amplitude has decreased slightly to 3.0 mV. The A/V ratio is now 1.0 where previously it was 0.5. Based on this data, it is diagnosed that the electrode (e.g., the P4 electrode) has moved to be in closer proximity to atrial tissue and further from ventricular tissue. Accordingly, an increase in the A wave amplitude and a decease in the V wave amplitude are seen.

In the example shown in FIG. 5, the A potential amplitude is expected to increase with dislodgement because the proximal electrode (P4) would be more proximal at the time of TEST_2 measurement than at the time of the BASELINE measurement. That is, the P4 electrode is in closer proximity to left atrial tissue than before. The V potential amplitude would remain the same or decrease depending on how far proximal the electrode is now situated. Further, it would help confirm dislodgement if the increase in A potential amplitude detected on the left ventricle lead occurred without a corresponding increase in the atrial amplitude detected on an right atrial lead.

If the A amplitude has remained the same or decreased, and the A/V ratio has increased, a change in the ventricular substrate (scar, new conduction abnormality, or other condition) is a likely cause. Dislodgement is not completely excluded, however, as explained below. In FIG. 6, again, the baseline data on the left shows 2.0 mV and 4.0 mV resulting in an A/V ratio of 0.5. On the right, the test data (TEST_3) shows that the atrial potential has not changed. It is still 2.0 mV. However, the peak ventricular potential has decreased to 3 mV. Additionally, the morphology of the potential has changed. On the left side of the trace, a healthy sharp potential is seen, indicating a quick activation. On the right side, a fractioned activation is seen, which typically indicates some conduction delays particularly in the vicinity of the electrode. The fractioned/activation has caused enough of a change in the A/V ratio to trigger a suspicion that the lead condition has changed. There is a change, but it cannot be determined whether a dislodgement or something else occurred from examination of the A/V ratio alone. Thus, the V morphology or the V amplitude or the V timing compared to the baseline data helps determine whether the lead has dislodged. In the example shown in FIG. 6, the morphology of the ventricular potential indicates it is likely the lead has not dislodged but rather some change in the underlying tissue near the ventricular electrode has occurred.

If the A amplitude has decreased and the A/V ratio has decreased, a change in the atrial substrate (scar, new conduction abnormality, etc) is suspected. Again, dislodgement is not completely excluded. In FIG. 7, again the baseline data is the same. In this example, a reduction in the A/V ratio is present. On the right side, the test data (TEST_4) shows the ventricular amplitude is constant at 4.0 mV but the atrial potential is now smaller at 1.0 mV. A diagnosis of an atrial substrate change and not a dislodgement may be appropriate.

Figure 6:
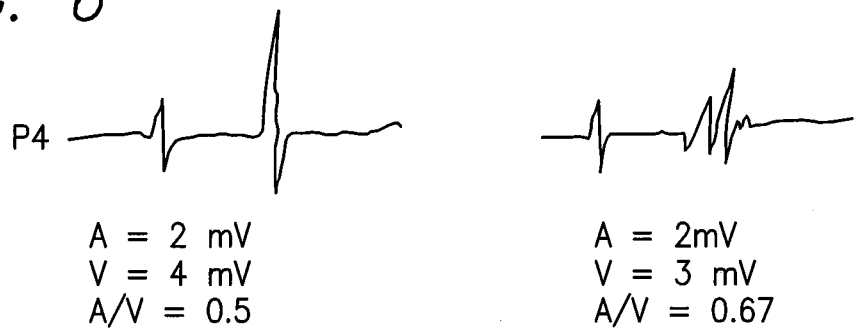
FIG. 6 is a diagram illustrating exemplary baseline and test intra cardiac electrograms, recorded from a left ventricular quad polar lead, showing atrial and ventricular potentials.
Figure 7:
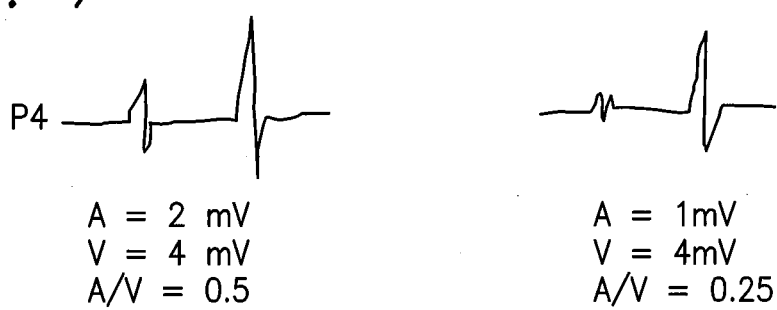
FIG. 7 is a diagram illustrating exemplary baseline and test intra cardiac electrograms, recorded from a left ventricular quad polar lead, showing atrial and ventricular potentials.

In the examples illustrated in FIGS. 6 and 7, a substrate changes are suspected, which could be confirmed by amplitude and/or morphology analysis of the suspect ventricular or atrial potentials. Other features, such as the time between the A and V potentials on the electrogram may also confirm a substrate change (e.g., new substrate would have slow ventricular conduction), as discussed below in more detail. In FIG. 7, an atrial substrate change is suspected, and may be confirmed by the amplitude and/or morphology analysis of the atrial potential, and/or by the timing between RA sense and the P4 sense or the relative count of A:V, particularly using another left ventricular electrode or right ventricular electrode for a "standard" V activation (e.g., decreased atrial amplitude due to atrial tachyarrhythmias/atrial fibrillation.) In addition, if the atrial activation on the RA lead and/or the P4 electrode is more frequently observed than on any lead showing ventricular activation, atrial tachyarrhythmia may be indicated. In either case, the size of A or V amplitude can be compared to the amplitude of a fixed lead, for example, the right atrial or right ventricular fixed leads, as such fixed leads should not experience potential amplitude changes due to dislodgment but rather only due to biologic processes (encapsulation, disease, etc). However, in the absence of these other confirmatory comparisons, dislodgement cannot be ruled out even when the A or V potentials remain the same or decrease, in that the coronary sinus has a region where left atrial potentials are not strongly sensed.

A set of thresholds should be set for both the A amplitude and the A/V ratio as for what is considered "same," "increase," and "decrease" states. Normal variability is expected across time, particularly during the lead maturation phase. Also, it is known that there is variability of electrogram amplitude over the respiratory cycle. By taking the average amplitude over several cardiac and respiratory cycles, or by using gating methods to store electrogram amplitudes only during a certain portion of the respiratory cycle, or by using gating methods to store electrogram amplitudes only when the patient is in certain postures (e.g. sitting, lying), or by using Kalman filtering or other space state analysis this variation could be reduced or eliminated from the measurements.

Although the examples described above compared the A wave test data with A wave template data recorded from the same electrode, the present disclosure is not so limited. For example, the data from one lead may be compared with data from a different lead. In one embodiment, the left heart P4 electrode data is compared with data recorded from a right atrial lead. In another embodiment, the A/V ratio is computed using data from different leads. For example, the A/V ratio could be computed based on A data from the left ventricle P4 electrode and from V data from the right atrial lead. In yet another embodiment, data from other electrodes on the same lead is used. For example, data recorded from the P4 electrode and data from the M3 electrode could be used to compare amplitudes and/or to calculate the A/V ratio. These alternate configurations could be used in addition to or instead of the single electrode data analyses discussed above. In one embodiment, such an alternate configuration may be employed as a secondary confirmation.

Figure 8:
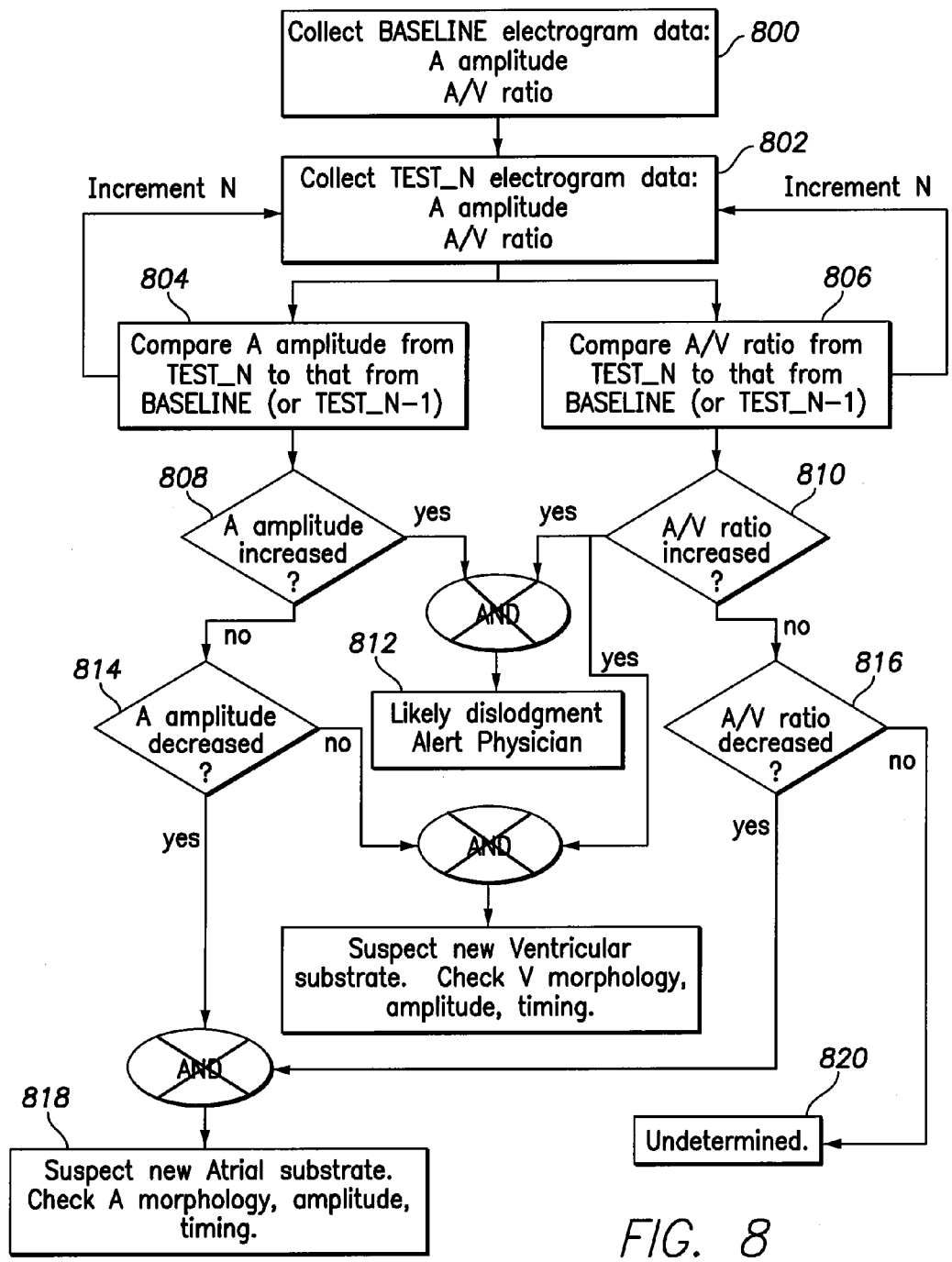
FIG. 8 is a functional block diagram illustrating functional blocks included in one embodiment of the present teachings.

Referring now to FIG. 8, a functional block diagram is shown illustrating functional blocks included in one embodiment of the present teachings. Note that amplitude generally refers not to single beat amplitude but rather average amplitude over several cardiac and respiratory cycles.

At block 800, the baseline data is collected. For example, atrial and ventricular amplitudes and the A/V ratio are collected. At block 802, the test electrogram data is collected. The test data may be collected either at regular intervals or when prompted by the physician.

At blocks 804 and 806, the test A amplitude and the baseline A amplitude are each individually compared with the A/V ratio. In other embodiments, the current test data and the prior test data (or multiple prior test data) are compared, rather than comparing with the baseline data, resulting in a running average.

If the A amplitude increases (at block 808) dislodgement is suspected. Thus, at block 810, it is determined whether the A/V ratio has increased. If both the A amplitude and the A/V ratio have increased, at block 812, a likely diagnosis of lead dislodgment is made, after which the physician may be alerted to consider additional testing (e.g., a chest X-ray or fluoroscopy) that can be performed to confirm whether the lead has dislodged.

If the A amplitude did not increase (block 808: NO), at block 814 it is determined whether the A amplitude has actually decreased. If so, atrial substrate growth is considered, i.e., there may be some atrial fibrillation or some atrial remodeling that caused the amplitude to now be smaller than it was previously. If the A/V ratio did not increase (block 810: NO), at block 816, it is determined whether the A/V ratio has decreased at block 816. If yes, and if the A amplitude decreased (814: YES), a new atrial substrate is suspected. In this case, at block 818, the A morphology, amplitude and/or timing are evaluated to help confirm whether a new atrial substrate has developed.

If the A/V ratio does not increase and does not decrease, meaning it stays the same, then the lead status is considered undetermined (block 820). If the A/V ratio has increased (810: YES), but the A amplitude has decreased (814: NO), then a ventricular substrate change is suspected at block 822. In this case, other discriminators are evaluated, such as morphology, amplitude, and/or timing to determine whether a new ventricular substrate exists.

In addition to a simple comparison of TEST_N data versus BASELINE data, in another embodiment, TEST_N data is compared with TEST_N−1 data to determine if any changes have occurred since the last follow-up, rather than since implantation. This type of comparison would be particularly helpful if other changes, with explanation other than lead dislodgment, are suspected. Further, trend data from BASELINE and including all TEST_N amplitudes and ratios may be generated to help fine-tune the threshold for detecting a dislodgment based on the trend.

Referring now to FIG. 9, an exemplary table of lead diagnoses is discussed. The table corresponds to the flow diagram of FIG. 8. More specifically, when an A amplitude has increased and the A/V ratio has increased, lead dislodgment may be diagnosed. When an A amplitude has decreased and the A/V ratio has decreased, a new atrial substrate may be suspected. When an A amplitude has not changed and the A/V ratio has increased, a new ventricular substrate may be suspected.

In another embodiment, a A/V ratio is analyzed in addition to or instead of the A/V ratio. For example, different electrodes on the quartet lead or one lead on the quartet lead on the left ventricle and one electrode from the right ventricle could be analyzed. In this embodiment, a morphology discriminator would be beneficial. If both potentials changed amplitude and the sharpness is the same, it is likely to have resulted from a lead dislodgement. If both potentials changed amplitude and each has a different morphology, then it is suspected that a substrate has developed.

As mentioned above, timing can be evaluated to help diagnose lead migration. For example, the A/V interval measured on a single electrode could indicate a lead has migrated. In this embodiment, it would be desirable to measure in the same rhythm, for example in a pace rhythm, from a pacing location other than the measurement electrode and at a constant AV delay at subsequent measurements in order to use that timing criteria validly. The time difference from the A potential to the V potential could be evaluated, for example, on the proximal electrode (P4). If the time difference increases despite having the A/V pace delay the same, a third reference is then evaluated. In one embodiment, the third reference is the time from either the atrial pacing or the right atrial potential to the sensed atrial potential on the left ventricle electrode.

In such conditions, two results are possible. One result is increased bi-atrial conduction time or slowed ventricular conduction (i.e., increased time from ventricular pace to ventricular sense at a distal location). The other result is lead migration. Given the same activation pattern in both the atria and the ventricle, because of measuring from different locations, the analysis is a little more involved. Thus, measuring occurs relative to some fiducial point(s), such as the right atrial pace, and the time difference between the atrial sense and ventricular activations on a single electrode are analyzed.

Figure 10:
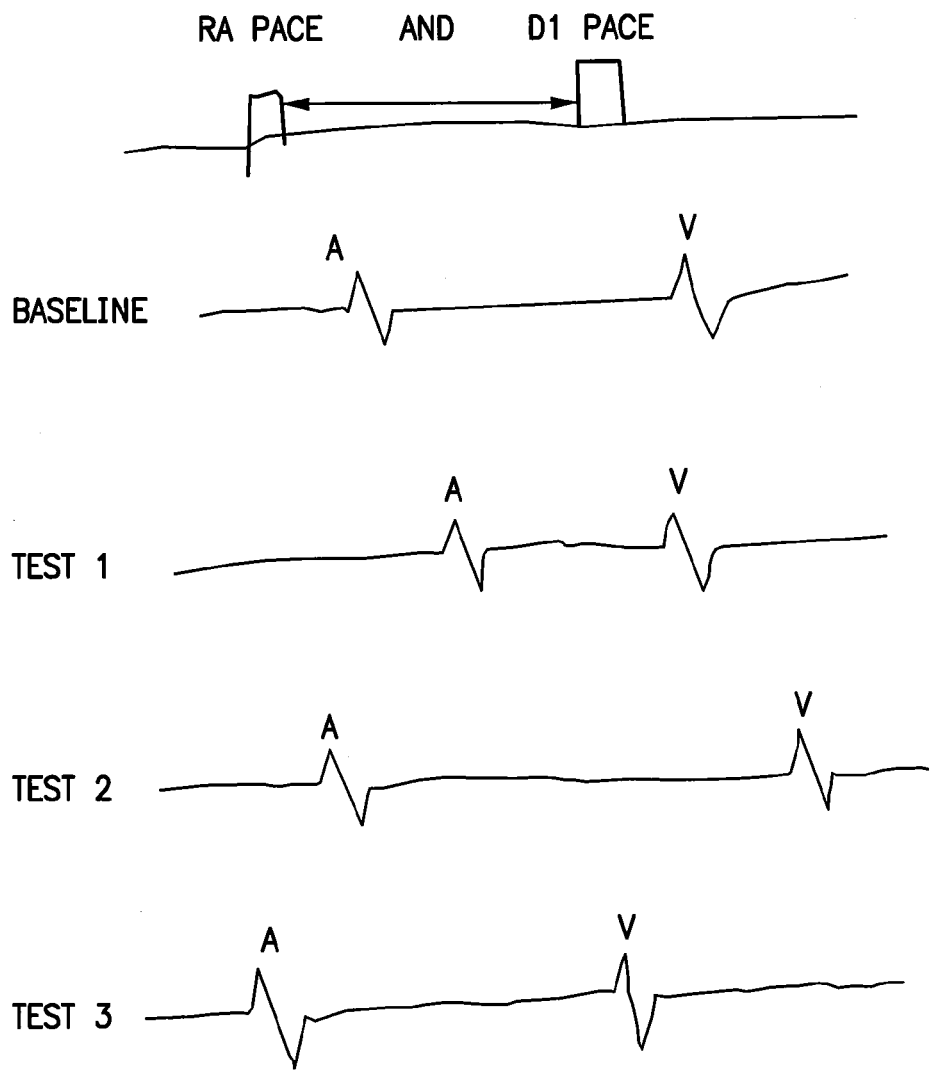
FIG. 10 is a diagram illustrating exemplary baseline and test intra cardiac electrograms, showing atrial and ventricular potentials.

Referring now to FIG. 10, an example will be provided with respect to the RA pace and the D1 pace as the fiducial points. The uppermost diagram shows the timing of when right atrial (RA) pacing occurs, the A/V delay (AVD), and when pacing from the D1 electrode occurs. Baseline data is then obtained with respect to an atrial (A) potential and a ventricular (V) potential, from for example the P4 electrode. Test data is later measured from the same electrode, for example the P4 electrode.

In a first test, it is observed that the test 1 atrial potential occurs later than the baseline atrial potential, whereas the ventricular potentials from the baseline and first test occur at approximately the same time. Such data indicates slow atrial conduction.

In a second test, it is observed that the test 2 atrial potential occurs at approximately the same time as the baseline atrial potential, whereas the test 2 ventricular potential occurs later than the baseline ventricular potential. Such data indicates slow ventricular conduction.

In a third test, it is observed that the test 3 atrial potential occurs earlier than the baseline atrial potential, and the test 3 ventricular potential occurs earlier than the baseline ventricular potential. Such data indicates lead migration. Alternately, if both the atrial and ventricular test potentials were to occur later than their respective baseline potentials, lead migration would also be indicated.

Referring back to FIG. 3, an A-V relationship is seen in terms of the timing of the events. As the electrode is closer to the AV groove or nearer the atrium, the far field potential will get closer to the source of the activation. As the electrode gets closer to the source of activation, the morphology of the far field potential becomes narrower and sharper. Looking at the atrial component from the right atrium, for example the proximal P4 electrogram, the A wave is closer to the right atria than in the M2 electrogram or even in distal D1 electrogram. The A potential recorded in this distal electrode D1 is between that A potential sensed by the M2 electrode and the ventricular activation.

In one embodiment, timing templates are created and stored. If it appears the A potential and the V potential are closer to each other in the test data than in the template, a dislodgement is suspected. In another embodiment, templates from different electrodes are compared. For example, it the timing of the M2 template is similar to the test data of the D1 electrode, it is possible the D1 electrode has moved to where the M2 electrode was previously located.

In still another embodiment, narrowing of the A wave could be interpreted as an indicator of a lead moving closer to the source of the activation. In other words, the A wave becomes less of a far field measurement and more of a near field measurement. Thus, a morphological analysis can help detect dislodgement. By evaluating the morphology of the A potential, i.e., the width of the A potential, it may be possible to diagnose whether the lead is moving closer to the atrium. In this embodiment, a narrower A potential indicates the lead is closer to the atrium.

In yet another embodiment, real time monitoring occurs during the implant procedure. Thus, lead migration during the implant procedure may be monitored. Moreover, lead migration could be evaluated after the implant procedure is completed, when the patient first stands up.

In another embodiment, the templates are patient posture-dependent. For example, a first template could be for when the patient is prone, a second template when the patient is sitting, a third template when the patient is upright, another template for resting, another for walking, etc.

In still another embodiment, NV modulation with respiration is evaluated. Such variance is largely based on contact of the electrode with the heart throughout the respiratory cycle. For example, baseline data may show that, from full inhalation to full expiration, A amplitude varies 50% and the V amplitude varies 35%. If, through the same respiratory cycle of full inhalation to full expiration, the atrial signal modulates 80% in amplitude (instead of 50%) and the ventricular signal modulates 60% in amplitude (instead of 35%), a dislodgment could be suspected. A template for each electrode on a lead is employed to facilitate diagnosis based on A/V modulation with respiration, according to one aspect. In another aspect, a confirmatory analysis occurs when the diagnosis based on A/V modulation indicates possible lead dislodgment.

Another embodiment of this disclosure considers the sudden appearance of A potentials on electrograms that previously did not have them, as a sign of gross left ventricle lead dislodgement. At the time of implant, the presence or lack of left atrial potentials on each of the left ventricle unipolar (or bipolar) sense electrograms is noted. At follow-up, or automatically at regular intervals, the sense configuration is temporarily programmed to each of the left ventricle unipolar (or bipolar) vectors, and each is tested for the presence or absence of A potential. If one or more vectors that previously lacked A potential now shows A potential, lead dislodgement is suspected. The larger the new A potentials, the more vectors on which new A potentials are present, and the greater the difference in V morphology or amplitude from baseline, the stronger the suspicion of dislodgement.

The methodologies described herein may be implemented by various means depending upon the application. For example, these methodologies may be implemented in hardware, firmware, software, or any combination thereof. For a hardware implementation, the processing units, including programmable microcontroller 60 (FIG. 2) may be implemented within one or more application specific integrated circuits (ASICs), digital signal processors (DSPs), digital signal processing devices (DSPDs), programmable logic devices (PLDs), field programmable gate arrays (FPGAs), processors, controllers, microcontrollers, microprocessors, electronic devices, other electronic units designed to perform the functions described herein, or a combination thereof.

For a firmware and/or software implementation, the methodologies may be implemented with modules (e.g., procedures, functions, and so on) that perform the functions described herein. Any machine or computer readable medium tangibly embodying instructions that may be in a form implantable or coupled to an implantable medical device may be used in implementing the methodologies described herein. For example, software code may be stored in a memory and executed by a processor. When executed by the processor, the executing software code generates the operational environment that implements the various methodologies and functionalities of the different aspects of the teachings presented herein. Memory may be implemented within the processor or external to the processor. As used herein the term "memory" refers to any type of long term, short term, volatile, nonvolatile, or other memory and is not to be limited to any particular type of memory or number of memories, or type of media upon which memory is stored.

The machine or computer readable medium that stores the software code defining the methodologies and functions described herein includes physical computer storage media. A storage medium may be any available medium that can be accessed by the processor of an implantable medical device. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. As used herein, disk and/or disc includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer readable media.

Although the present teachings and its advantages have been described in detail, it should be understood that various changes, substitutions and alterations can be made herein without departing from the spirit and scope of the present teachings as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present teachings, processes, machines, manufacture, compositions of matter, means, methods, or steps, presently existing or later to be developed that perform substantially the same function or achieve substantially the same result as the corresponding embodiments described herein may be utilized according to the present teachings. Accordingly, the appended claims are intended to include within their scope such processes, machines, manufacture, compositions of matter, means, methods, or steps.

What is claimed is:

1. A method for evaluating an implanted electrical lead condition, the method comprising:
   sensing a test electrogram having test atrial cardiac potentials and test ventricular cardiac potentials using an electrode coupled to the implanted electrical lead;
   comparing one or more features of an atrial template with one or more features of the test atrial potentials;
   comparing one or more features of a ventricular template with one or more features of the test ventricular potentials;
   comparing the one or more features of the test atrial potentials to the one or more features of the test ventricular potentials; and
   determining the implanted electrical lead condition based on the comparison of the one or more features of the atrial template with one or more features of the test atrial potentials, the comparison of the one or more features of the ventricular template with one or more features of the test ventricular potentials, and the comparison of the test atrial potentials and test ventricular potentials.

2. The method of claim 1, in which the compared test electrogram features and template electrogram features comprise atrial amplitudes and ventricular amplitudes.

3. The method of claim 2, further comprising sensing the compared test electrogram features and electrogram template features with a quad polar lead.

4. The method of claim 2, in which the compared test electrogram features and electrogram template features comprise features for a plurality of different patient postures.

5. The method of claim 2, in which the compared test electrogram features and electrogram template features comprise features modulating with respiration.

6. The method of claim 1, in which the test electrogram features and the template electrogram features comprise timing between atrial and ventricular events.

7. The method of claim 1, in which the electrogram template features are collected when the implanted electrical lead is known to be in a correct position.

8. An implantable medical device (IMD) comprising:
   an electrical lead having an electrode adapted to sense atrial cardiac potentials and to measure ventricular cardiac potentials;
   a programmable microcontroller coupled to the electrical lead, the programmable microcontroller controlling operation of the IMD;
   a memory coupled to the programmable microcontroller, the memory storing an atrial electrogram template and a ventricular electrogram template; and
   a lead condition analysis module stored in the memory, wherein, when executed by the programmable microcontroller, the lead condition analysis module configures the IMD:
      to measure a test electrogram having test atrial cardiac potentials and test ventricular cardiac potentials using the electrode;
      to compare one or more features of the atrial electrogram template with one or more features of the test atrial potentials;
      to compare one or more features of the ventricular electrogram template with one or more features of the test ventricular potentials;
      to compare the one or more features of the test atrial potentials to the one or more features of the test ventricular potentials; and
      to determine an electrical lead condition based on the comparison of the one or more features of the atrial electrogram template with one or more features of the test atrial potentials, the comparison of the one or more features of the ventricular electrogram template with one or more features of the test ventricular potentials, and the comparison of the test atrial potentials and test ventricular potentials.

9. The IMD of claim 8, in which the compared test electrogram features and template electrogram comprise atrial amplitudes and ventricular amplitudes.

10. The IMD of claim 9, further comprising sensing the compared test electrogram features and electrogram template with a quad polar lead.

11. The IMD of claim 9, in which the compared test electrogram features and electrogram template comprise features for a plurality of different patient postures.

12. The IMD of claim 9, in which the compared test electrogram features and electrogram template comprise features modulating with respiration.

13. The IMD of claim 8, in which the test electrogram features and the template electrogram features comprise atrial morphological features and ventricular morphological features.

14. The IMD of claim 8, in which the test electrogram features and the template electrogram features comprise timing between atrial and ventricular events.

15. A system for evaluating an implanted electrical lead condition, the system comprising:
- means for measuring a test electrogram having test atrial cardiac potentials and test ventricular cardiac potentials using an electrode coupled to the implanted electrical lead;
- means for comparing one or more features of an atrial electrogram template with one or more features of the test atrial potentials;
- means for comparing one or more features of a ventricular electrogram template features with one or more features of the test ventricular potentials;
- means for comparing the one or more features of the test atrial potentials to the one or more features of the test ventricular potentials; and
- means for determining the implanted electrical lead condition based on the comparison of the one or more features of the atrial electrogram template with one or more features of the test atrial potentials, the comparison of the one or more features of the ventricular electrogram template with one or more features of the test ventricular potentials, and the comparison of the test atrial potentials and test ventricular potentials.

16. The system of claim 15, in which the compared test electrogram features and template electrogram features comprise atrial amplitudes and ventricular amplitudes.

17. The system of claim 16, further comprising sensing the compared test electrogram features and electrogram template features with a quad polar lead.

18. The system of claim 16, in which the compared test electrogram features and electrogram template features comprise features for a plurality of different patient postures.

19. The system of claim 16, in which the compared test electrogram features and electrogram template features comprise features modulating with respiration.

* * * * *